United States Patent
Maly et al.

[11] Patent Number: 5,378,254
[45] Date of Patent: Jan. 3, 1995

[54] FILTER SENSING APPARATUS AND FILTER THEREFOR

[75] Inventors: Edward C. Maly, Hartland; Alireza Bemanian, Milwaukee; John D. Bryson, Jr., Pewaukee, all of Wis.

[73] Assignee: Vaportek, Inc., Sussex, Wis.

[21] Appl. No.: 138,584

[22] Filed: Oct. 15, 1993

[51] Int. Cl.⁶ ............................................. B01D 46/42
[52] U.S. Cl. ........................................ 55/271; 55/274
[58] Field of Search ................................. 55/274, 271

[56] References Cited

U.S. PATENT DOCUMENTS

| | | | |
|---|---|---|---|
| 3,201,772 | 8/1965 | Ladusaw | 55/274 |
| 3,399,516 | 9/1968 | Hough, Jr. et al. | 55/274 |
| 3,718,982 | 3/1973 | Deaton | 55/274 |
| 3,745,965 | 7/1973 | Ljung et al. | 55/274 |
| 3,785,556 | 1/1974 | Watkins . | |
| 3,874,146 | 4/1975 | Watkins . | |
| 3,885,737 | 5/1975 | Watkins . | |
| 3,923,934 | 12/1975 | Watkins . | |
| 4,040,042 | 8/1977 | Mayer | 55/274 |

FOREIGN PATENT DOCUMENTS

| | | | |
|---|---|---|---|
| 0132619 | 7/1985 | Japan | 55/271 |
| 1033210 | 2/1986 | Japan | 55/271 |
| 3093319 | 4/1988 | Japan | 55/274 |
| 3147514 | 6/1988 | Japan | 55/274 |
| 2048013 | 2/1990 | Japan | 55/271 |

OTHER PUBLICATIONS

Vaportek Brochure "The Optimum 1000 Environmental Odor Controller", Vaportek, Sussex, Wisc. 53089.

*Primary Examiner*—Tim Miles
*Attorney, Agent, or Firm*—Quarles & Brady

[57] ABSTRACT

An air treatment system has a removable and replaceable filter, the filter having a plastic frame, and having a multi-layer filtering medium. A filter seat has a switch located along one side in contact with a flexible tab. When the filter is located in the seat and faces the desired direction, one of two projections on the top and bottom of the filter frame moves the flexible tab to activate the switch, which signals proper installation of the filter. When a filter element is installed, it starts a timer which times the service life of the filter element and an air treatment cartridge. When the timer times out, it signals a user through an LED or audible alarm to replace the replaceable components.

8 Claims, 4 Drawing Sheets

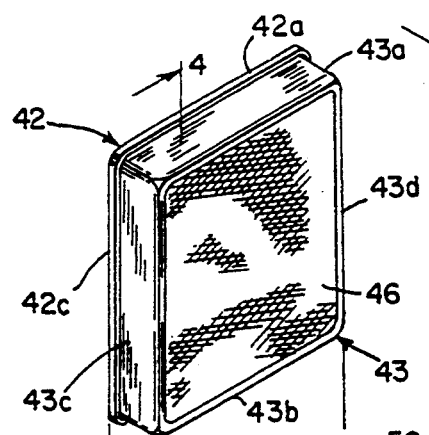
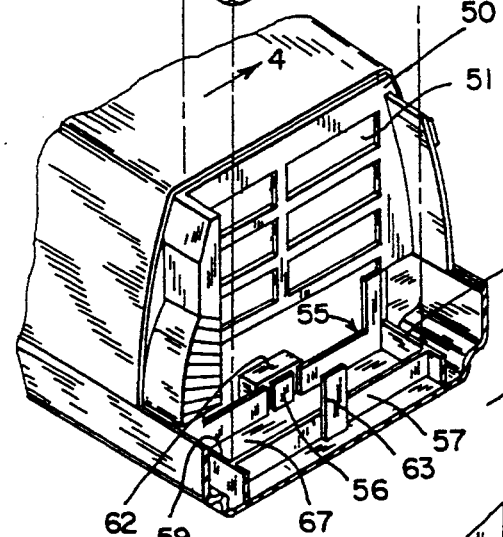
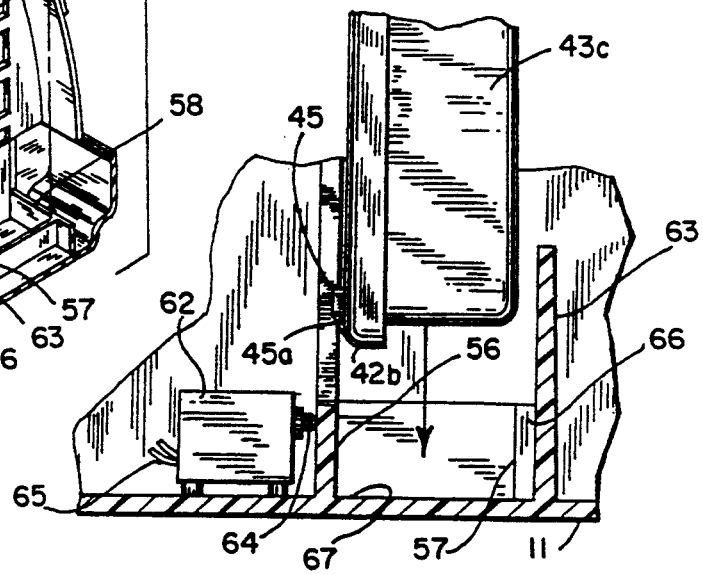
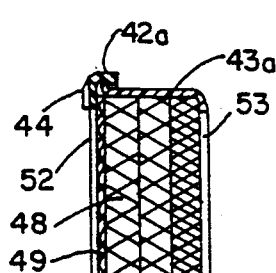
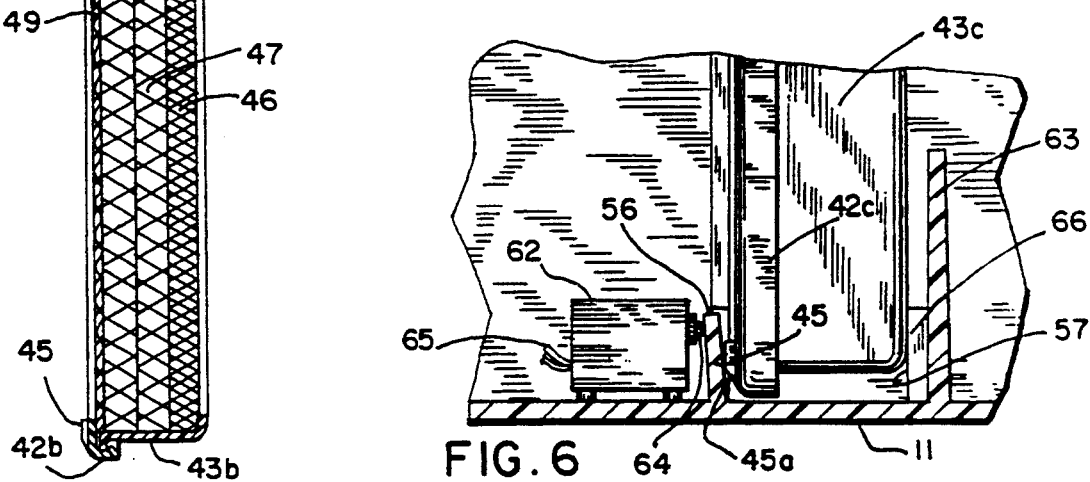

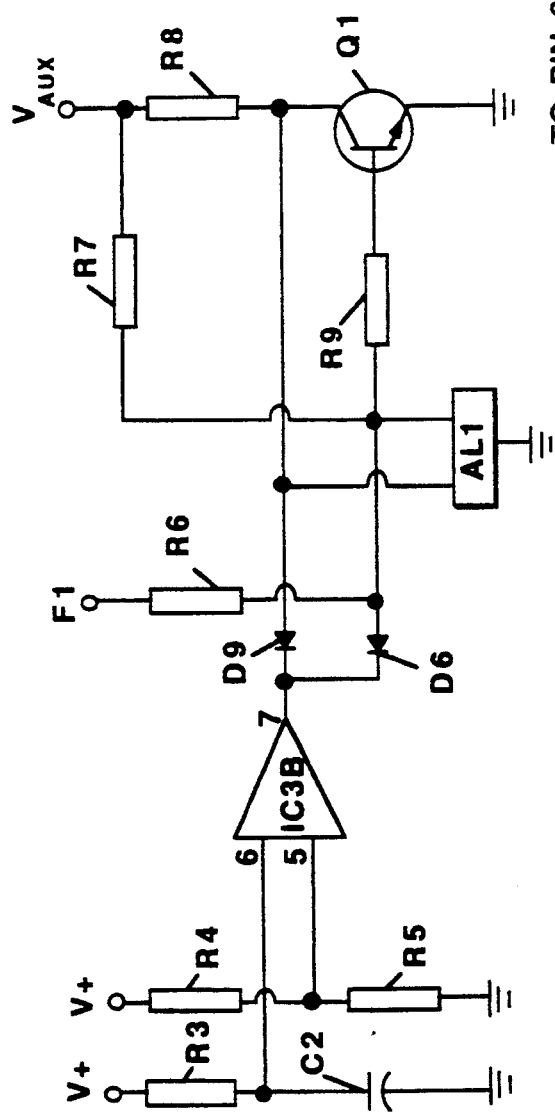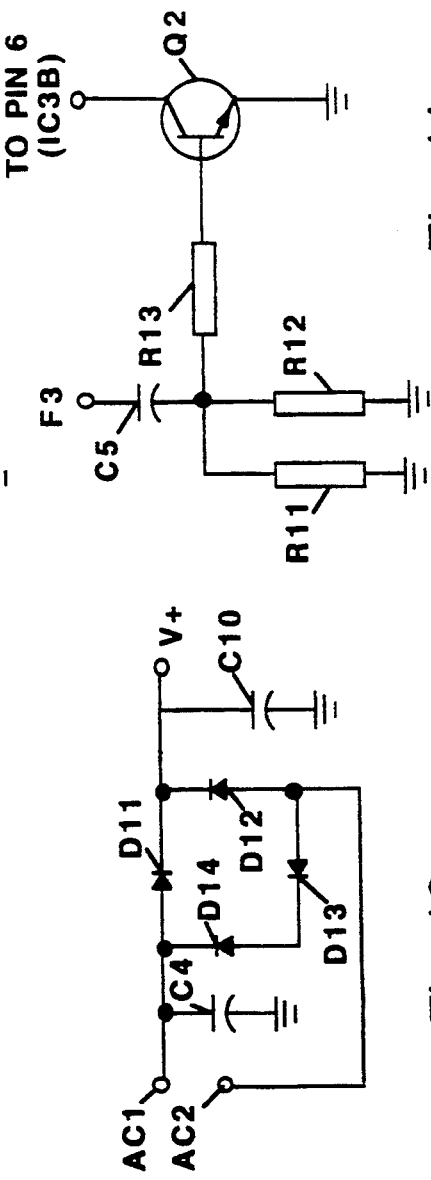

FILTER SENSING APPARATUS AND FILTER THEREFOR

TECHNICAL FIELD

The invention relates to small, portable vaporizing equipment for dispensing liquids into the air to improve the quality of the air.

BACKGROUND ART

Various types of vaporizing apparatus have been known for treating air. Watkins, U.S. Pat. No. 3,923,934, issued Dec. 2, 1975, shows a device for vaporizing a liquid into the air to control odors. Such a device is more broadly applicable to the dispensing of liquids, including odorants, deodorants, and air fresheners.

The Watkins device uses a vaporizing element, which is described in further detail in Watkins, U.S. Pat. No. 3,885,737, issued May 27, 1975.

In prior devices of this type, replacement of the vaporizing element was based on observation by the user, either of the time of usage, or the effectiveness of the vaporizing cartridge. It would be advantageous to assist customers in determining when to replace, not only the vaporizing element, but also any other replaceable elements, such as air filters, in such units.

SUMMARY OF THE INVENTION

The invention relates to an air treatment system having an air processing element, a seat for receiving and holding the air processing element in an operating position, a switch located adjacent one side of the seat, and an electronic control that is electrically connected to the switch to signal the proper installation of the air processing element in the seat.

While in a preferred embodiment the air processing element is an air filter, the invention can be applied to other types of air processing elements, including a vaporizing element. In the present invention, the signal for the air filter is also used to signal the condition of the vaporizing element.

The invention also relates to a specific type of air filter element having a frame and a filter medium within the frame, and at least one projection on the frame for operating the switch when the filter is positioned in the seat to assure proper front-and-back orientation of the filter relative to the direction of air flow.

In a further aspect of the invention, projections are located on both the top and bottom cross members and face the same direction to assure activation of the switch upon location of either cross member in the filter seat with the projection facing the switch. This prevents operation of the switch when the filter is inserted facing away from the switch. Thus, the up-and-down orientation of the filter will not prevent switch operation. However, an incorrect front-to-back orientation relative to the direction of air flow will be sensed as absence of the filter.

The electronic control includes a timer that is responsive to the positioning of the filter element in the seat to begin a timing cycle representing the service life of an individual filter. A signaling device is controlled by the electronic control to signal an observer, through a visual and an audible alarm, when the timing cycle has been completed.

The alarm may be used to signal replacement of both the air filter and a vaporizing cartridge element.

The sensing system assures proper installation of the air filter element, as well as timely replacement of the air filter and the vaporizing cartridge.

Other objects and advantages, besides those discussed above, will be apparent to those of ordinary skill in the art from the description of the preferred embodiment that follows. In the description, reference is made to the accompanying drawings, which form a part hereof, and which illustrate examples of the invention. Such examples, however, are not exhaustive of the various embodiments of the invention, and, therefore, reference is made to the claims which follow the description for determining the scope of the invention.

BRIEF DESCRIPTION OF THE DRAWINGS

FIG. 3 is a perspective, exploded view showing the filter apparatus of the present invention;

FIG. 4 is a sectional view taken in the plane indicated by line 4—4 in FIG. 3;

FIG. 5 is a detail view showing a first position of a switch prior to being operated by the filter of FIGS. 3 and 4;

FIG. 6 is a detail view showing a second position of the switch as it is operated by the filter of FIGS. 3 and 4:

FIGS. 7, 8, 9, 10 and 11 are circuit diagrams of the electronics employed in the apparatus of FIG. 1.

DETAILED DESCRIPTION OF THE PREFERRED EMBODIMENT

Figure 1:
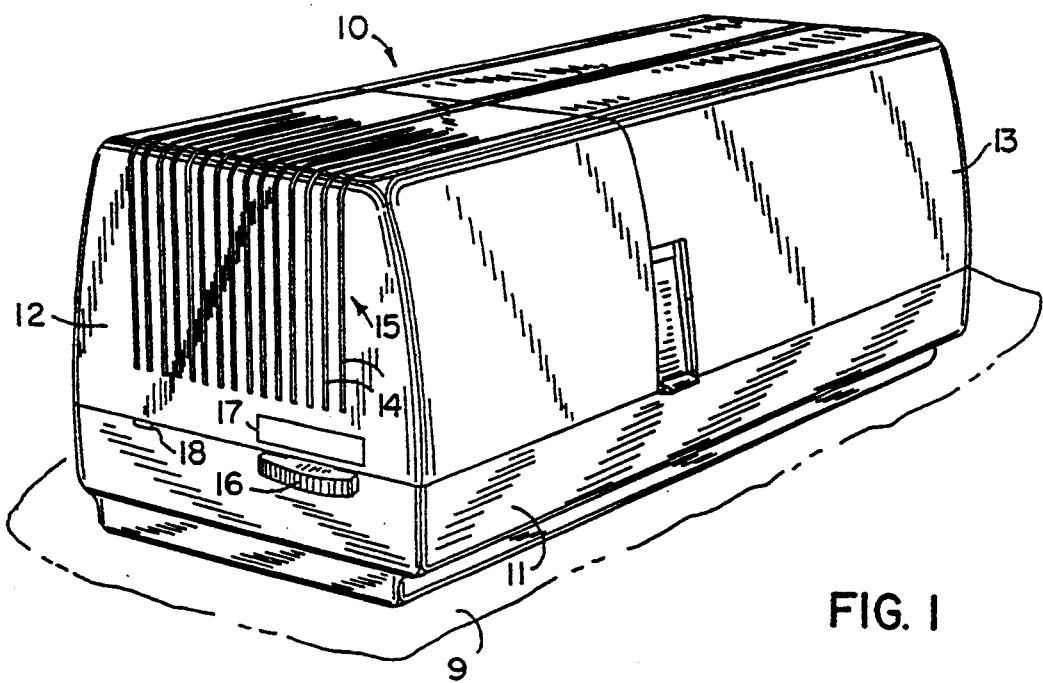
FIG. 1 is a perspective view of the front end of an apparatus incorporating the present invention.

FIG. 1 shows an air treatment system 10 that incorporates the present invention. The apparatus 10 includes an exterior housing having three main parts: a base or chassis 11, a front end cover 12 and a rear end cover 13. The chassis 11 is supported by external supporting surface 9. The front end cover 12 includes spaced parallel vents 14 forming a grille 15 for venting vaporized air into the environment. On the front side of cover 12 are blower switch member 16 and LED 18. A legend 17 is positioned over the switch to provide visual symbols corresponding to switch positions such as: POWER ON, POWER OFF, FAN HI SPEED and FAN LOW SPEED. An audible alarm (not shown in FIG. 1) is located inside the housing.

Figure 2:
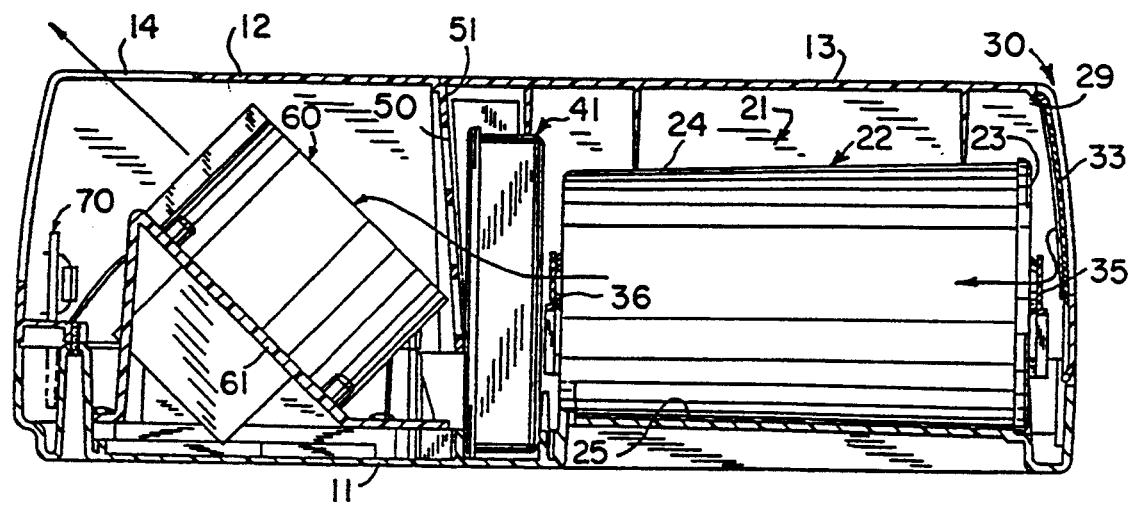
FIG. 2 is a longitudinal sectional view of the apparatus of FIG. 1.

Referring next to FIG. 2, a replaceable vaporizing cartridge 21 is disposed on its side. The cartridge 21 includes a canister 22 with a disc-shaped cover 23 and a cylindrical bottom member 24, the cover 23 facing towards vents 29 formed at the rear end of the apparatus 10 (FIG. 3). The canister 22 is supported in a longitudinal trough within a cradle 25 that is formed as an integral part of the chassis 11. By replacing the entire cartridge 21, it becomes unnecessary to handle an air processing element within the canister 22. For further description of the vaporizing element, reference is made to Watkins, U.S. Pat. No. 3,885,737, issued May 27, 1975. For further description of the air flow control and vaporizing cartridge 21, reference is made to a copending application of Bryson et al., Ser. No. 08/137,655, filed Oct. 19, 1993, entitled "Air Flow Control System With Replaceable Cartridge," and filed on even date herewith.

The front grille 15 extends along the front and part of the top side of the front cover 12. The rear grille 30 has a number of parallel vents 29 (FIG. 2), similar to the front vents 14. The rear grille 30 stops approximately where the top face meets the rear face of the rear cover 13. As seen in FIG. 2, a first filter 33 is mounted in channels integrally formed with the rear cover 13 just inside the rear vents 29.

As illustrated in FIG. 2, by the arrows, untreated air flows in through rear vents 29 and filter 33 into inlet port 35 in the cartridge cover 23. Vapor-laden air flows out of an outlet port 36 at the other end of the canister 22. The vapor-laden air then flows through a second filter 41 and vents 50 in a rear wall 51 of the front housing cover 12, the air being drawn by the suction created by a fan 60. The fan 60 is mounted in an inclined position on support 61. The fan 60 exhausts vapor-laden air at an upward angle through front vents 14. A circuit board 70 carrying electronic circuitry is mounted on edge near the front of the housing. This circuitry 70 controls the fan motor 60 in response to operation of the switch 16 seen in FIG. 1. The circuitry on circuit board 70 is also connected to user signaling devices, such as the LED 18 on the front and the audible alarm (not shown in FIG. 2).

Referring to FIGS. 3-6, a service life timer for the filter 41 and vaporizing cartridge 21 is controlled by insertion and removal of the filter 41. The filter 41 (FIG. 4) more particularly includes a frame with a front cover 42 and back member 43. Front cover 42 has top and bottom cross members 42a, 42b and right and left side members 42c, 42d. As used herein, "left" and "right" are as seen from the front of the dispenser in FIG. 1. Similarly, back member 43 has top and bottom cross members 43a, 43b and right and left side members 43c, 43d. Cover 42 and member 43 are each integrally formed of plastic. On the top and bottom cross members 42a, 42b of cover 42, a pair of projections 44, 45 (FIGS. 4, 5, 6) are integrally formed. These are located midway between right and left side members 42c, 42b. The projections have a taper as they extend downward, identified by reference 45a in FIG. 5, for reasons that will become more apparent from the explanation below.

The multi-stage filter 41 contains three different media to remove smoke, dust and pollen. As seen in FIG. 4, there is first filter layer 46 of relatively coarse, more densely woven filter material. Two layers 47 and 48 are sandwiched between layer 46 and another layer 49. Layers 47 and 48 are made of filter material of less dense weave and less coarse than layer 46, while layer 49 is made of a thin, fine, closely woven material, resembling fine gauze. These layers 46, 47, 48 and 49 are held between cover 42 and member 43, each of which have respective large rectangular openings 52 and 53 for allowing air to flow through the back and out the front of the filter 42.

Referring to FIG. 3, the filter 41 is received in a rectangular filter seat formed by floor 67, front side wall 55, back side wall 57, left end wall 58 and right end wall 59 ("left" and "right" as seen from the front of the apparatus 10 in FIG. 1). An upright flexible tab 56 is formed on chassis 11 midway along wall 55. As seen in FIGS. 5 and 6, when the filter 41 is positioned correctly in the seat, the projection 45 will push tab 56 and further push in a button 64 on a microswitch 62. This microswitch 62 preferably includes gold-plated contacts to assure operation after 3-month intervals corresponding to the life cycle of the replaceable elements. The microswitch 62 is connected by leads 65 to circuit 70 seen in FIG. 1. When the microswitch 62 is not activated the contacts are closed. With the filter in place, the microswitch 62 is activated to open the switch contacts. With the filter 41 removed or facing the wrong direction, the contacts of switch 62 will remain closed. Upright 63 is provided to back up a gap 66, which is left to receive the projections 44, 45 if the filter 41 is installed facing the wrong direction. If this gap 66 were not provided, it may be possible for the tab 56 to be bent by the tight fit of the filter frame, irrespective of the direction in which the projections 44, 45 were facing.

Projections 44, 45 are located on both the top and bottom cross members facing a common direction to assure activation of the switch 62 upon location of either one of the top and bottom cross members 42a, 42b in the filter seat with a respective projection facing the switch 62, while preventing operation of the switch 62 when inserted facing away from the switch.

The following is a description of the electrical circuitry which connects to microswitch 62 and which controls operation of LED 18 and an audible alarm AL1, the latter being represented schematically in FIG. 9. When the air treatment system 10 is turned on, an audible alarm emits a series of beeps or chirps to confirm correct operation of the electrical circuitry. The LED 18 will turn on and remain on. When the electronic control senses that it is time to replace the replaceable elements, it will cause the LED 18 to flash and the alarm will sound at some regular interval. When the filter 41 is replaced in the filter seat, a reset operation will occur to reset the circuitry for another timing cycle. When the air treatment system 10 is turned on again, the audible alarm again emits a series of beeps or chirps, and the LED is turned on, to again confirm correct operation of the electrical circuitry.

Referring to FIGS. 7, 8, 9, 10 and 11, a timing circuit is provided for timing a period of days extending approximately three (3) months, which is the period set for replacement of the air filter 41 and vaporizing cartridge 21.

Figure 7:
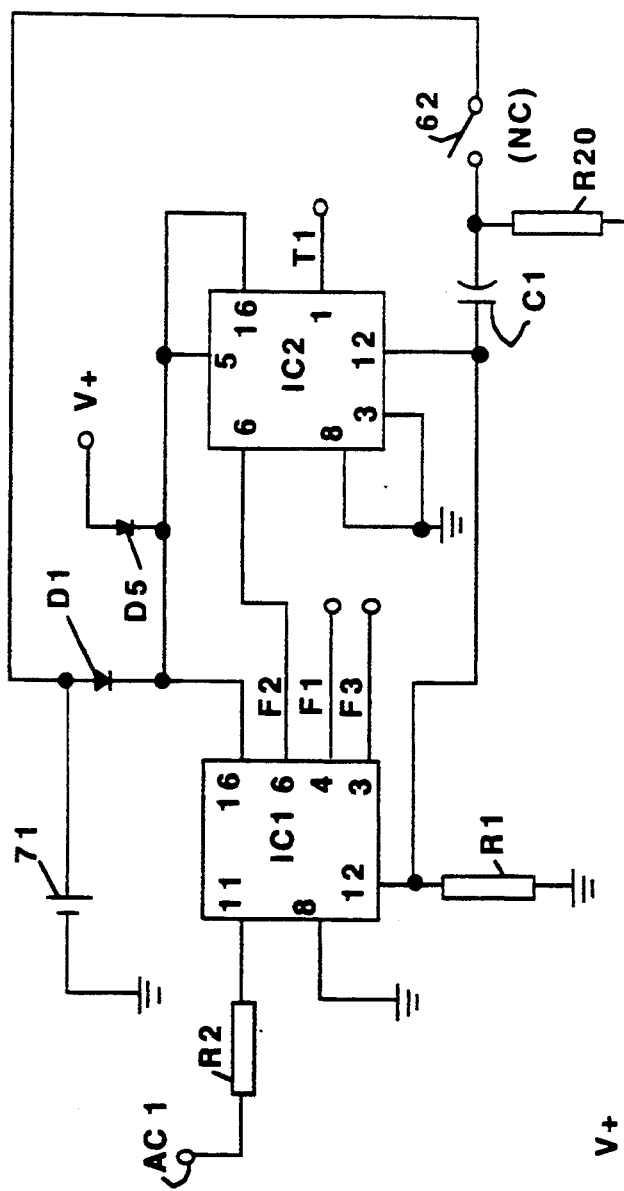

FIG. 7 shows the timing circuit which includes two integrated circuits IC1 and IC2. Commercial circuits such as MC14060 and MC14521 counter circuits, available from Motorola, are suitable for use as integrated circuits IC1 and IC2, respectively. The timing circuit operates in response to the 60 Hz frequency from the AC power input AC 1 in FIG. 7.

As further seen in FIG. 7, an AC signal at 60 Hz is received through resistor R2 at "pin 11" of IC1. A very low frequency signal F2, a fraction of 1 Hz, is transmitted from "pin 6" on IC1 to "pin 6" on IC2. Circuit IC2 acts as a counter that emits a signal T1 from "pin 1" at the end of a period of days approximating three (3) months.

Circuit IC1 also transmits a signal F1 from "pin 4". This signal is used to control the rate of beeping of the audible alarm on power on and the rate of flashing of the LED 18 when the timing circuit times out. Circuit IC1 also transmits signal F3 from "pin 3". This becomes an input to the reset circuit in FIG. 11, which produces an output to pin 6 of IC3B to operate the audible alarm on each "power on" or reset.

Power from DC power supply V+ is provided through diode D5 to IC1 and IC2 at "pin 16". A battery 71 is connected to the same pins through diode D1. The two diodes provide a switching operation. With AC power applied, the higher voltage of the DC power supply V+ will be provided to "pin 16". When AC power is switched off, to replace the filter 41, for example, the circuits IC1 and IC2 are supplied by DC power from the battery 71.

The circuits IC1 and IC2 are reset by operation of NC (normally closed) switch, which is the microswitch 62 described earlier. This switch 62 is normally closed, when no filter 41 is located in the filter seat. With the insertion of the filter 41, the switch 62 is opened.

IC3A (FIG. 8) and IC3B (FIG. 9) are two operational amplifiers provided in a package available commercially as the LM358 integrated circuit from National Semiconductor. These circuits more directly control the operation of the LED 18 (FIG. 8) and the audible alarm AL1 (FIG. 9).

Figure 8:
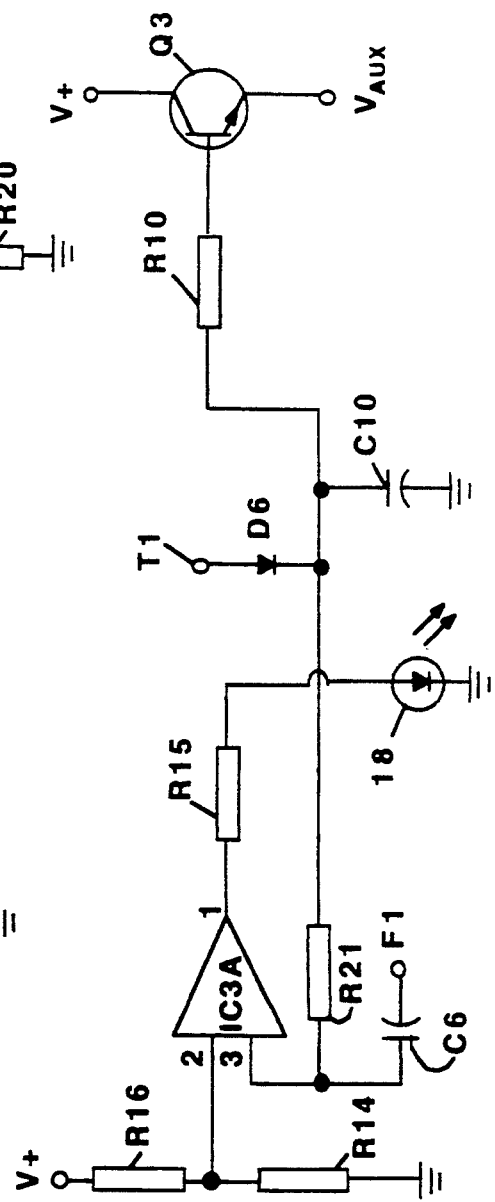

Referring first to FIG. 8, a voltage is applied to "pin 2" of IC3A by a biasing circuit of resistors R14 and R16, which receives DC supply signal V+. This produces an output signal at "pin 1" which turns on LED 18. When the voltage at "pin 3" is changed relative to "pin 2", this will cause a change of the output signal at "pin 1" to switch off LED 18. If the voltage at "pin 3" oscillates back and forth, this will cause the LED 18 to blink "off" and then "on" again.

To provide this blinking operation, "pin 3" of IC3A is connected through capacitor C6 to receive the flashing rate frequency signal F1. Normally, however, this signal is masked by biasing resistor R21 connected in parallel with capacitor C6 to "pin 3". When time-out signal T1 is applied through diode D6 and resistor R21 to "pin 3" on IC3A, this allows signal F1 to control the switching of IC3A and the flashing of LED 18 at the flash rate F1.

Normally, signal T1 is low, thereby keeping off transistor Q3 in FIG. 8. When signal T1 goes to a certain positive voltage, transistor Q3 is turned on through resistor R10, and DC signal, V+, is connected to output $V_{aux}$. Referring to FIG. 9, the $V_{aux}$ becomes a power signal to supply audible alarm AL1 through resistor R7 and R8. The alarm AL1 can be made to sound intermittently in response to signal F1 applied through resistor R6. As long as the pin 7 output of op amp IC3B is high, the alarm can be controlled by the $V_{aux}$ power signal and signal F1.

Op amp IC3B controls the sounding of the audible alarm AL1. As seen in FIG. 9, resistor R9 and transistor Q1 form an oscillator circuit for alarm circuit AL1. Resistors R7 and R8 provide a circuit by which signal $V_{AUX}$ is provided to power the alarm circuit AL1, when signal T1 is present in FIG. 8. Diodes D9 and D6 provide a disable circuit when the output of IC3B is low. The op amp IC3B has biasing resistors R3, R4 and R5 connected to its inputs at "pin 6" and "pin 5". Capacitor C2 is connected to "pin 6" and provides a 10-second delay in audible sounds.

DC power for the above circuitry is provided by a power supply circuit seen in FIG. 10. AC power at 8-10 volts is applied to terminals AC1 and AC2. Capacitor C4 works in conjunction with resistor R2 in FIG. 7 to control the clock signal into "pin 11" of IC 1. Diodes D11, D12, D13 and D14 form a full-wave rectifying bridge for converting an AC signal into a DC signal. Capacitor C10 filters signal the V+ output signal from the diode bridge. The output of the circuit of FIG. 10 is a DC supply signal, V+.

The network in FIG. 11 of capacitor C5, resistors R13, R11, R12 and transistor Q2 is a reset circuit that will cause the audible alarm to be operated when the unit is turned on. After a certain time signal F3 from "pin 3" on IC1 is applied through capacitor C5 and resistor R13 to turn on transistor Q2, which will pull pin 6 low on IC3B and cause a reset signal from its output "pin 7" for operating audible alarm AL1, which is then operated at frequency F1.

Thus, it has been described and shown how the circuitry of FIGS. 7-11 accomplishes the functions of the invention in response to the insertion and removal of the filter 41.

This has been a description of examples of how the invention can be carried out. Those of ordinary skill in the art will recognize that various details may be modified in arriving at other detailed embodiments, and these embodiments will come within the scope of the invention.

Therefore, to apprise the public of the scope of the invention and the embodiments covered by the invention, the following claims are made.

We claim:

1. An air treatment system for processing air that passes therethrough, wherein the air treatment system further comprises;

an air processing element;

a seat for receiving and holding the air processing element in an operating position;

a switch located adjacent the seat, the switch being operable in response to the positioning of the air processing element in the seat; and an electronic control that is electrically connected to the switch to signal proper installation of the air processing element in the seat;

wherein the seat is formed by two spaced apart side walls and two spaced apart end walls in a space between the side walls, one of the side walls including means in contact with the switch;

wherein the air processing element includes a frame with at least one projection for moving the means in contact with the switch to operate the switch when the air processing element is positioned in the seat; and wherein the projection is located on one face of the frame to assure proper front-and-back orientation of the air processing element relative to a direction of air flow through the air processing element.

2. The air treatment system of claim 1, wherein the switch is a microswitch with gold-plated contacts.

3. The air treatment system of claim 1, wherein the electronic control includes a timer that is responsive to the positioning of the air processing element in the seat to begin a timing cycle representing the service life of an individual air processing element; and a signaling device that is controlled by the electronic control to signal an observer when the timing cycle has been completed.

4. The air treatment system of claim 3, wherein the signaling device emits an audible sound.

5. The air treatment system of claim 3, wherein the signaling device emits light.

6. An air treatment system for processing air that passes therethrough, wherein the air treatment system further comprises:

an air processing element:

a seat for receiving and holding the air processing element in an operating position;

a switch located adjacent the seat, the switch being operable in response to the positioning of the air processing element in the seat; and an electronic control that is electrically connected to the switch to signal proper installation of the air processing element in the seat;

wherein the seat is formed by two spaced apart side walls and two spaced apart end walls in a space between the side walls, one of the side walls including means in contact with the switch;

wherein the frame of the air processing element has spaced crossmembers; and wherein projections are located on both the cross members and face a common direction to assure activation of the switch upon location of either cross member in the seat with the projections facing the switch.

7. An air filter for an apparatus having means for holding the filter in an operating position, switch means located adjacent said holding means, and an electronic control that is electrically connected to the switch means for sensing proper installation of a filter element in the filter seat, the air filter comprising:

a frame and a filter medium within the frame;

wherein said frame of the filter includes at least one projection for operating the switch means when the filter is positioned in said holding means; and wherein the filter frame has front and back faces and wherein a projection is located on one of the front and back faces to assure proper front-and-back orientation of the filter relative to air passing through it.

8. The air filter of claim 7, wherein the frame of the filter has top and bottom cross members spaced apart, the top and bottom cross members each having front and back faces; and wherein projections are located on both the top and bottom cross members on at least one of the front and back faces, the projections facing a common direction to assure activation of the switch upon location of either one of the top and bottom cross members in the filter seat with a respective projection facing the switch, while preventing operation of the switch when the filter is inserted facing away from the switch.

* * * * *